(12) United States Patent
Rajamani et al.

(10) Patent No.: US 9,797,819 B2
(45) Date of Patent: Oct. 24, 2017

(54) SENSOR FOR TENSION MEASUREMENT

(71) Applicant: Regents of the University of Minnesota, Minneapolis, MN (US)

(72) Inventors: Rajesh Rajamani, Saint Paul, MN (US); Kalpesh Singal, Glenville, NY (US)

(73) Assignee: Regents of the University of Minnesota, Minneapolis, MN (US)

( * ) Notice: Subject to any disclaimer, the term of this patent is extended or adjusted under 35 U.S.C. 154(b) by 924 days.

(21) Appl. No.: 13/789,431

(22) Filed: Mar. 7, 2013

(65) Prior Publication Data
US 2013/0238257 A1 Sep. 12, 2013

Related U.S. Application Data

(60) Provisional application No. 61/608,475, filed on Mar. 8, 2012.

(51) Int. Cl.
| | |
|---|---|
| *G01L 1/14* | (2006.01) |
| *G01L 5/00* | (2006.01) |
| *G01N 3/20* | (2006.01) |
| *G01N 3/08* | (2006.01) |
| *G01L 1/04* | (2006.01) |

(52) U.S. Cl.
CPC .................. *G01N 3/08* (2013.01); *G01L 1/04* (2013.01); *G01L 1/142* (2013.01); *G01L 5/0038* (2013.01); *G01N 3/20* (2013.01)

(58) Field of Classification Search
CPC ......... G01L 1/04; G01L 1/142; G01L 5/0038; G01N 3/20; G01N 3/08
See application file for complete search history.

(56) References Cited

U.S. PATENT DOCUMENTS

| | | | | |
|---|---|---|---|---|
| 4,058,008 A | * | 11/1977 | Pilkington | ............. B65H 59/40 73/862.473 |
| 4,888,945 A | * | 12/1989 | Maeda | ................. D01H 13/005 57/264 |
| 5,433,116 A | * | 7/1995 | Ahlstrom | ............... G01N 3/066 177/229 |

(Continued)

FOREIGN PATENT DOCUMENTS

WO    WO/2010/118117    * 10/2010

OTHER PUBLICATIONS

P. Peng et al., "Novel MEMS stiffness sensor for force and elasticity measurements", Department of Mechanical Engineering, University of Minnesota, 111 Church Street SE, Minneapolis, MN 55455, USA, © 2009 Elsevier B.V., pp. 10-17.*

(Continued)

*Primary Examiner* — Alexander Satanovsky
(74) *Attorney, Agent, or Firm* — Shumaker & Sieffert, P.A.

(57) ABSTRACT

A device includes a first sensor and a second sensor. The first sensor is configured to generate a first signal corresponding to a detected first force. The second sensor is configured to generate a second signal corresponding to a detected second force. The first force and the second force has a substantially common direction. The device includes a processor configured to determine a measure of tension using the first signal and using the second signal. The measure of tension corresponds to displacement of an elongate member.

10 Claims, 3 Drawing Sheets

(56) References Cited

U.S. PATENT DOCUMENTS

| | | | | |
|---|---|---|---|---|
| 5,877,434 | A * | 3/1999 | Sturm | B65H 59/40 |
| | | | | 73/862.391 |
| 5,980,246 | A * | 11/1999 | Ramsay | A61C 7/06 |
| | | | | 433/5 |
| 6,274,953 | B1 * | 8/2001 | Hwang | H02P 6/006 |
| | | | | 310/12.19 |
| 2008/0184819 | A1 * | 8/2008 | Morimoto | G01L 5/165 |
| | | | | 73/862.626 |
| 2012/0041345 | A1 * | 2/2012 | Rajamani | A61B 5/103 |
| | | | | 600/587 |
| 2013/0338627 | A1 * | 12/2013 | Rylander | A61M 5/158 |
| | | | | 604/501 |

OTHER PUBLICATIONS

Ahmad et al., "Biomechanics of Shoulder Capsulorrhaphy Procedures," J. Shoulder Elbow Surg., vol. 14(12S), Jan.-Feb. 2005, 9 pp.

Ahn et al., "Second-look Arthroscopic Findings of 208 Patients after ACL reconstruction," Knee Surg. Sports Traumatol. Arthrosc., vol. 15(242), Mar. 2007, pp. 242-248.

Arneja et al., "Graft Tensioning in Anterior Cruciate Ligament Reconstruction: A Systematic Review of Randomized Controlled Trials," Arthroscopy, vol. 25(2), Feb. 2009, 10 pp.

Arnold et al., "ACL Graft Can Replicate the Normal Ligament's Tension Curve," Knee Surg, Sports Traumatol. Arthrosc., vol. 13(8), Nov. 2005, pp. 625-631.

Arnold et al., "The Remains of Anterior Cruciate Ligament Graft Tension After Cyclic Knee Motion," Am. J. Sports Med., vol. 33(4), Apr. 2005, 9 pp.

Bae et al, "Indentation Testing of Human Articular Cartilage: Effects of probe tip geometry and Indentation Depth on Intra-Tissue Strain," J. Biomech, vol. 39(6), Apr. 2005, 11 pp.

Barry et al., "Design and Performance of a Modified Buckle Transducer for the Measurement of Ligament Tension," J. Biomech. Eng., vol. 108(2), May 1986, 6 pp.

Belanger et al., "Hemocompatibility, Biocompatibility, Inflammatory and in Vivo Studies of Primary Reference Materials Low-Density Polyethylene and Polydimethylsiloxane: A Review," J. Biomed. Mater. Res., vol. 58(5), Jun.-Aug. 2001, 12 pp.

Beringer et al., "An Overview of Economic Issues in Computer-Assisted Total Joint Arthroplasty," Clin. Orthop. Relat. Res., vol. 463, Oct. 2007, 6 pp.

Brenneke et al., "Glenohumeral Kinematics and Capsulo-Ligamentous Strain Resulting from Laxity Exams," Clin. Biomech., vol. 15(10), Dec. 2000, 10 pp.

Brown et al., "Dynamic Performance Characteristics of the Liquid Metal Strain Gage," J. Biomech., vol. 19(2), 1986, 11 pp. (Note: Applicant points out in accordance with MPEP 609.04(a) that the 1986 year of publication is sufficiently earlier than the effective U.S. filing date and any foreign priority date of Mar. 7, 2013 so that the particular month of publication is not in issue.).

Caprise et al., "Open and Arthroscopic Treatment of Multidirectional Instability of the Shoulder," Arthroscopy, vol. 22(10), Oct. 2006, 8 pp.

Cross et al., "Measurements of String Tension in a Tennis Racket," Sports Engineering, vol. 4(3), Aug. 2001, 13 pp.

Cuomo et al, "The Effects of Different Tensioning Strategies on Knee Laxity and Graft Tension after Double-bundle Anterior Cruciate Ligament Reconstruction," Am. J. Sports Med., vol. 35(12), Dec. 2007, 10 pp.

Dalton et al., "Complications of Achilles and Posterior Tibial Tendon Surgeries," Clin. Orthop. Relat. Res., vol. 391, Oct. 2001, 9 pp.

D'Lima et al. "An ABJS Best Paper: Dynamic Intraoperative Ligament Balancing for Total Knee Arthroplasty," Clin. Orthop. Relat. Res., vol. 463, Oct. 2007, 6 pp.

Engebretsen et al., "The Effect of an Iliotibial Tenodesis on Intraarticular Graft Forces and Knee Joint Motion," The American Journal of Sports Medicine; vol. 18(2), Apr. 1990, 9 pp.

Erdemir et al., "Influence of Loading Rate and Cable Migration on Fiberoptic Measurement of Tendon Force," J. Biomech., vol. 35(6), Jun. 2002, 8 pp.

Fleming et al., "Determination of a Zero Strain Reference for the Anteromedial Band of the Anterior Cruciate Ligament," Journal of Orthopaedic Research, vol. 12(6), Nov. 1994, 8 pp.

Fletcher et al., "The Physics of Musical Instruments," Springer, Second Edition, 1998, 15 pp. (Note: Applicant points out in accordance with MPEP 609.04(a) that the 1998 year of publication is sufficiently earlier than the effective U.S. filing date and any foreign priority date of Mar. 7, 2013 so that the particular month of publication is not in issue.).

Frank et al., "The Science of Reconstruction of the Anterior Cruciate Ligament," J. Bone Joint Surg. Am., vol. 79, Oct. 1997, 22 pp.

Franta et al., "The Complex Characteristics of 282 Unsatisfactory Shoulder Arthroplasties," J. Shoulder Elbow Surg., vol. 16(5), Sep./Oct. 2007, 10 pp.

Grover et al., "Early Tension Loss in an Anterior Cruciate Ligament Graft: A Cadaver Study of Four Tibial Fixation Devices," J. Bone Joint Surg., vol. 87(2), Feb. 2005, 10 pp.

Hanley et al,, "Load Sharing and Graft Forces in ACL Reconstructions With the LAD," Am. J. Sports Med., vol. 17(3), Jun. 1989, 11 pp.

Hayes et al., "Shoulder Instability: Management and Rehabilitation," J. Orthop. Sports Phys. Ther., vol. 32(10), Oct. 2002, 14 pp.

Heis et al., "Tensioning of the Anterior Cruciate Ligament Graft," Ortho. Clin. North Am., vol. 33(4), Oct. 2002, 5 pp.

Hunter et al., "Graft Force-Setting Technique in Reconstruction of the ACL," Am. J. Sports Med., vol. 18(1), Feb. 1990, 9 pp.

In et al., "Agreements Between Different Methods of Gap Balance Estimation in Cruciate-retaining Total Knee Arthroplasty," Knee Surg, Sports Traumatol, Arthrosc., vol. 17, Jan. 2009, 7 pp.

Ishii et al., "Comparison of Joint Position Sense After Total Knee Arthroplasty," J. Arthroplasty, vol. 12(5), Aug. 1997, 6 pp.

Ishii et al., "Extramedullary vs. Intramedullary Alignment Guides in Total Knee Arthroplasty," Clin. Orthop. Relat. Res., vol. 318, Sep. 1995, 11 pp.

Janmey et al., "Dealing with Mechanics: Mechanisms of Force Transduction in Cells," Trends Biochem. Sci., vol. 29(7), Jul. 2004, 9 pp.

Kondo et al., "Second-look Arthroscopic Evaluations of Anatomic Double-bundle Anterior Cruciate Ligament Reconstruction: Relation with Postoperative Knee Stability" Arthroscopy, vol. 23(11), Nov. 2007, 13 pp.

Kristal et al., "A Method for Measuring Tension in Small Ligaments: An Application to the Ligaments of the Wrist Carpus," J. Biomech. Eng., vol. 115(3), Aug. 1993, 9 pp.

Kroner et al., "The Epidemiology of Shoulder Dislocations," Arch. Orthop. Trauma Surg., vol. 108(5), Aug. 1989, 4 pp.

Leondes, "Musculoskeletal Models and Techniques: Biomechanical Systems Techniques and Applications," CRC Press, vol. III, 2001, 7 pp. (Note: Applicant points out in accordance with MPEP 609.04(a) that the 2001 year of publication is sufficiently earlier than the effective U.S. filing date and any foreign priority date of Mar. 7, 2013 so that the particular month of publication is not in issue.).

Longjohn et al., "Soft Tissue Balance of the Hip," Arthroplasty, vol. 13(1), Jan. 1998, 5 pp.

Lundberg et al., "In Vivo Forces During Remodeling of a Two-Segment Anterior Cruciate Ligament Graft in a Goat Model," J. Orthop. Res., vol. 15(5), Jul. 1997, 8 pp.

Lynch et al., "Nonlinear Tension Observers for Web Machines," Automatica, vol. 40(9), Sep. 2004, 10 pp.

Lyyra et al., "In Vivo Characterization of Indentation Stiffness of Articular Cartilage in the Normal Human Knee," J. Biomed. Mater. Res., vol. 48(4), Jul. 1999, 7 pp.

Lyyra et al., "Indentation Instrument for the Measurement of Cartilage Stiffness Under Arthroscopic Control," Med. Eng. Phys., vol. 17(5), Jul. 1995, 6 pp.

Mae et al., "Optimization of Graft Fixation at the Time of Anterior Cruciate Ligament Reconstruction, Part II: Effect of Knee Flexion Angle," Am. J. Sports Med., vol. 36(6), Jun. 2008, 8 pp.

(56) References Cited

OTHER PUBLICATIONS

Mao et al., "In Vivo Nanomechanical Imaging of Blood-Vessel Tissues Directly in Living Mammals Using Atomic Force Microscopy," Appl. Phys. Lett., vol. 95(1), Jul. 2009 4 pp.

Mason et al., "Meta-analysis of Alignment Outcomes in Computer-Assisted Total Knee Arthroplasty Surgery," J. Arthroplasty, vol. 22(8), Dec. 2007, 12 pp.

Matsueda et al., "Soft Tissue release in Total Knee Arthroplasty: Cadaver Study Using Knees without Deformities," Clin. Orthop. Relat. Res., vol. 366, Sep. 1999, 11 pp.

Matziolis et al., "A Prospective, Randomized Study of Computer-Assisted and Conventional Total Knee Arthroplasty: Three Dimensional Evaluation of Implant Alignment and rotation," J. Bone Joint Surg. Am., vol. 89(2), Feb. 2007, 9 pp.

Mohanty et al., "Pressure Mapping at Orthropaedic Joint Interfaces with Fiber Bragg Gratings," Appl. Phys. Lett., vol. 88(8), Feb. 2006, 4 pp.

Mullhall et al., "Current Etiologies and Modes of Failure in Total Knee Arthroplasty Revision," Clin. Orthop. Relat. Res., vol. 446, May 2006, pp. 45-50.

Omori et al., "Contact Pressure and Three-dimensional Tracking of Unresurfaced Patella in Total Knee Arthroplasty," The Knee, vol. 4(1), Mar. 1997, 9 pp.

Pathak et al., "A Rate-controlled Indentor for in Vivo analysis of Residual Limb Tissues," IEEE Transactions on Rehabil. Eng., vol. 6(1), Mar. 1998, 11 pp.

Qu et al., "Calibrated Fluorescence Imaging of Tissue in vivo," Appl. Phys. Lett., vol. 78(25), Jun. 2001, 4 pp.

Rosenberger et al., "Improved Accuracy of Component Alignment with the Implementation of Image-Free Navigation in Total Knee Arthroplasty," Knee Surg. Sports Traumatol. Arthrosc., vol. 16, Mar. 2008, 11 pp.

Sabra et al., "Passive In Vivo Elastography from Skeletal Muscle Noise," Appl. Phys. Lett., vol. 90(19), May 2007, 4 pp.

Salmons, "The Eighth International Conference on Medical and Biological Engineering," Bio. Med. Eng., vol. 4(10), Oct. 1969, 10 pp.

Shino et al., "Graft Fixation with Predetermined Tension Using a New Device, the Double Spike Plate," Arthroscopy, vol. 18(8), Oct. 2002, 5 pp.

Sikorski, "Alignment in Total Knee Replacement," J. Bone Joint Surg. Br., vol. 90(9), Sep. 2008, 7 pp.

Singal et al., "Handheld Magnetic Sensor for Measurement of Tension," University of Minnesota, 11 pp.

Smith et al., "intraoperative Force-Setting did not Improve the Mechanical Properties of an Augmented Bone-Tendon-Bone Anterior Cruciate Ligament Graft in a Goat Model," J. Orthop. Res., vol. 14(2), Mar. 1996, 8 pp.

Tzima et al., "A Mechanosensory Complex that Mediates the Endothelial Cell Response to Fluid Shear Stress," Nature, vol. 437, Sep. 2005, 7 pp.

Wyss et al., "Tension Controlled Ligament Balanced Total Knee Arthroplasty: 5-year Results of a Soft Tissue Orientated Surgical Technique," Arch. Orthop. Trauma Surg., vol. 128, Feb. 2008, 9 pp.

* cited by examiner

SENSOR FOR TENSION MEASUREMENT

CLAIM OF PRIORITY

This application claims the benefit of priority to U.S. Patent Application Ser. No. 61/608,475, filed Mar. 8, 2012, the entire disclosure of which is hereby incorporated by reference herein in its entirety.

BACKGROUND

In orthopedic surgery, surgeons handle and manipulate bone and the surrounding soft tissue, including muscle, fascia, tendon, ligament and capsule. For some surgical procedures, successful handling of tissues and establishing proper tensile forces in the tissue is often the key to high reproducibility, good soft tissue healing, restoration of overall limb function in the patient, and a long lasting implant. However, methods for measuring soft tissue tension during surgery are inadequate. Current tissue tension measurement methods require either a violation of the soft-tissue (e.g. buckle transducer), or access to a free end of the tissue (e.g. graft tensioner).

OVERVIEW

The present inventors have recognized, among other things, that a problem to be solved can include accurately measuring soft tissue tension. An example of the present subject matter can help provide a solution to tension measurement when access is restricted to one side of the tissue and the ends of the tissue are fixed. One solution to this problem includes a handheld tool that is configured to provide a measure of force and displacement at three points along a filament or other tissue. Force and displacement measurement information is processed using an algorithm executed by a processor to yield a measure of tension.

The tissue can include a ligament, a filamentous tissue, or other elongate member.

An example of the present subject matter includes a device configured for measuring tension in a string, a ligament, a tissue, or other elongate member. The device can be handheld or carried by a robotic arm. An analytical formulation for measurement of tension is described.

By gently pushing the device against the elongate member, the tension in the member can be determined. An example device is approximately a centimeter in length and utilizes three force sensors. A force sensor can include a pin configured for axial movement in a channel. The pin can be urged to return to an at-rest position in the channel by an elastic member, such as a spring, and can cause a corresponding movement of a magnet. A magnetic field detector, such as a Hall effect detector, can provide an output signal corresponding to the magnet position, and thus, the position of the pin.

Some examples of surgical procedures that can benefit from improved tension measurement as described herein include total knee arthroplasty (TKA), patella dislocation, tendon repair, hip replacement, anterior cruciate ligament (ACL) repair, shoulder stabilization, and other orthopedic surgical procedures.

In addition, the present subject matter can be used for tension measurement in non-medical applications. Examples include web-handling processes (such as manufacturing), music (stringed instruments), and sports (tennis racquets).

An example of the present subject matter does not rely on an inertial reference, does not rely on access to opposing sides of a filament, and does not entail attachment or bonding to the string for measuring tension.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 2A and 2B illustrate a device for tension measurement, according to one example.

DETAILED DESCRIPTION

Figure 1A:
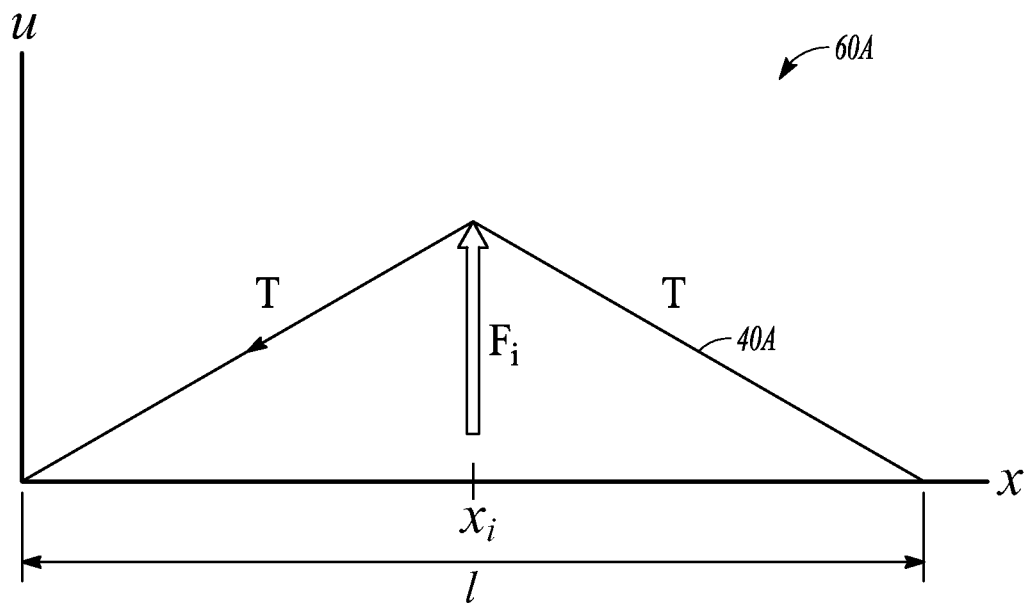
FIG. 1A illustrates a model for tension measurement, according to one example.

FIG. 1A illustrates model 60A for tension measurement, according to one example. In the figure, string 40A is under tension T.

The equation of displacement of string 40A under tension T is stretched on the x axis between fixed points x=0 and x=1, under a transverse per unit force given by f(x) is given by Equation (1).

$$-T\frac{d^2u}{dx^2} = f(x) \quad (1)$$

Equation (1) can be solved for a point force ($F_i$) acting at point $x_i$, as shown in FIG. 1A, and the deflection (u) of string 40A at any point x is then given by Equation (2).

$$u(x/x_i) = \frac{F_i}{T} \times \begin{pmatrix} \frac{(l-x_i)x}{l}; & 0 \leq x < x_i \\ \frac{(l-x)x_i}{l}; & x_i \leq x < l \end{pmatrix} \quad (2)$$

For three point forces acting at points $x_1$, $x_2$ and $x_3$, by superposition principle the displacements at these points are given by Equation (3):

$$\begin{bmatrix} u(x_1) \\ u(x_2) \\ u(x_3) \end{bmatrix} = \frac{1}{T} \times \begin{bmatrix} \frac{(l-x_1)x_1}{l} & \frac{(l-x_2)x_1}{l} & \frac{(l-x_3)x_1}{l} \\ \frac{(l-x_2)x_1}{l} & \frac{(l-x_2)x_2}{l} & \frac{(l-x_3)x_2}{l} \\ \frac{(l-x_3)x_1}{l} & \frac{(l-x_3)x_2}{l} & \frac{(l-x_3)x_3}{l} \end{bmatrix} \times \begin{bmatrix} F(x_1) \\ F(x_2) \\ F(x_3) \end{bmatrix} \quad (3)$$

According to one example, a device includes three sensors (sometimes referred to as bump) having pistons that move in slots. In one example, each slot is fitted with a spring that compresses as the piston moves in the slot.

The stiffness of the side bumps are equal to $K_s$, while that of the center bump is equal to $K_c$. According to one example, the three bumps are equidistant with the center-to-center distance between the adjacent bumps equal to d.

Figure 1B:
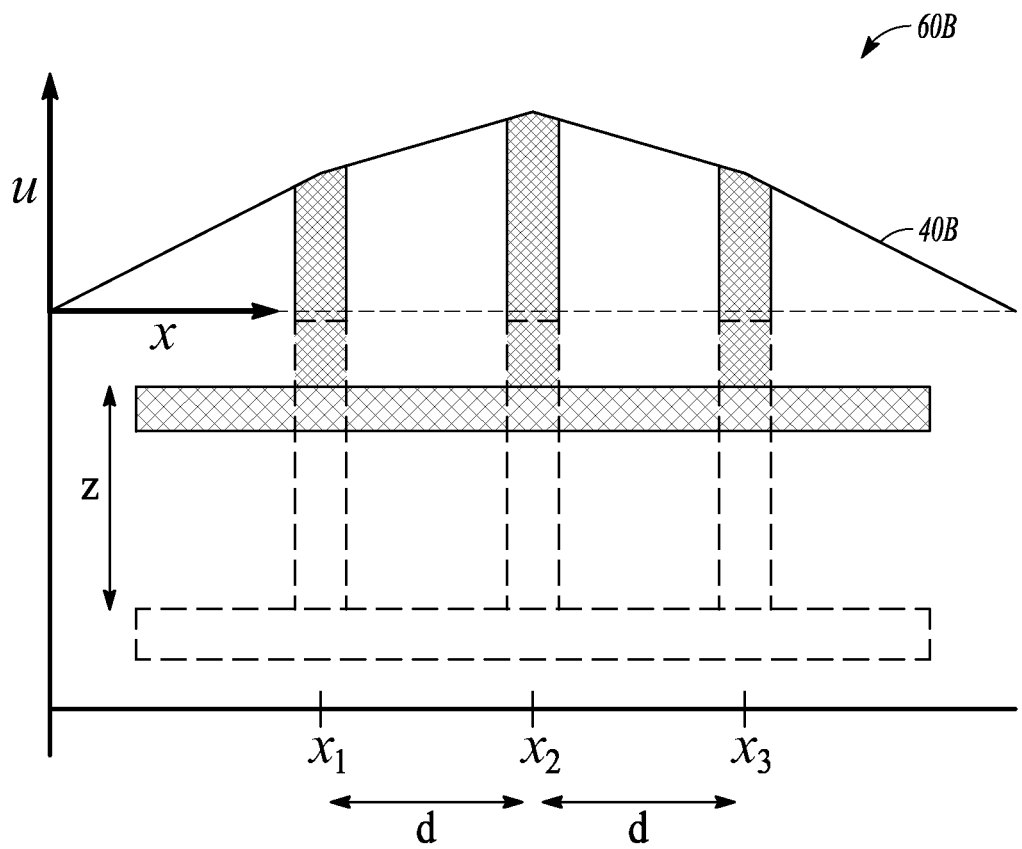
FIG. 1B illustrates a schematic of a device for tension measurement, according to one example.

FIG. 1B illustrates schematic 60B of a device for measuring tension in string 40B, according to one example. In the figure, the dashed lines denote the undeflected string and sensor and the solid lines denote the deflected string 40B and sensor.

Thus from the geometry of the sensor, $$x_1 = x_2 - d \quad (4)$$

$$x_3 = x_2 + d \quad (5)$$

Substituting Equations (4) & (5) in Equation (3), yields $$\begin{bmatrix} u(x_1) \\ u(x_2) \\ u(x_3) \end{bmatrix} = \frac{1}{T} \times \quad (6)$$

$$\begin{bmatrix} \frac{(l-(x_2-d))(x_2-d)}{l} & \frac{(l-x_2)(x_2-d)}{l} & \frac{(l-(x_2+d))(x_2-d)}{l} \\ \frac{(l-x_2)(x_2-d)}{l} & \frac{(l-x_2)x_2}{l} & \frac{(l-(x_2+d))x_2}{l} \\ \frac{(l-(x_2+d))(x_2-d)}{l} & \frac{(l-(x_2+d))x_2}{l} & \frac{(l-(x_2+d))(x_2+d)}{l} \end{bmatrix} \times \begin{bmatrix} F(x_1) \\ F(x_2) \\ F(x_3) \end{bmatrix}$$

Equation (6) can be re-written as, $$U = A_1 f \quad (7)$$
where $$A_1 = \frac{1}{T} \times \quad (8)$$

$$\begin{bmatrix} \frac{(l-(x_2-d))(x_2-d)}{l} & \frac{(l-x_2)(x_2-d)}{l} & \frac{(l-(x_2+d))(x_2-d)}{l} \\ \frac{(l-x_2)(x_2-d)}{l} & \frac{(l-x_2)x_2}{l} & \frac{(l-(x_2+d))x_2}{l} \\ \frac{(l-(x_2+d))(x_2-d)}{l} & \frac{(l-(x_2+d))x_2}{l} & \frac{(l-(x_2+d))(x_2+d)}{l} \end{bmatrix}$$

The compression in any of the three bumps under the applied normal force can be modeled as a linear spring, using:

$$F_i = K_i \times Y_i \quad (9)$$

where $Y_i$ is the compression of the spring under the bump i.

Assuming a normal contact and hence same displacement of the base of the three bumps, the compression in the springs under the bumps can be modeled as:

$$Y = Z - U \quad (10)$$

where Z is the displacement of the base of the three bumps, which under the assumption of normal contact can be treated as a constant for all three bumps. Assuming constant base deformation, Z can be written as $$Z = \begin{bmatrix} z \\ z \\ z \end{bmatrix} \quad (11)$$

Substituting Equations (9) and (10) in Equation (7), yields $$(I + A_1 K)Y = Z \quad (12)$$

where K is the stiffness matrix of the combined system and is equal to $$K = \begin{bmatrix} K_s & 0 & 0 \\ 0 & K_c & 0 \\ 0 & 0 & K_s \end{bmatrix} \quad (13)$$

The compressions (Y) in the springs, for any base displacement (Z), can be obtained by solving Equation (12). Assuming that $(I + A_1 K)$ is non-singular, the solution to Equation (12) is given in Equation (14).

$$Y = \frac{z}{\det(I + A_1 K)} \begin{bmatrix} \dfrac{-K_c K_s d^3 + T^2 l + K_s d^2 (K_c(l - x_2) - 2T) +}{T^2 l} \\ \dfrac{Td(K_c + 2K_s)(l - x_2)}{T^2 l} \\ \dfrac{Tl + K_s d(l - 2d)}{Tl} \\ \dfrac{-K_c K_s d^3 + T^2 l + K_s d^2(K_c x_2 - 2T) +}{T^2 l} \\ \dfrac{Td(K_c + 2K_s)x_2}{T^2 l} \end{bmatrix} \quad (14)$$

Substituting values from Equation (14), it can be shown that the ratio of displacement of the center bump to the average displacement of side bumps is given by Equation (15). This ratio is referred to as the response of the device.

$$R = \frac{Y_2}{(Y_1 + Y_3)/2} = \frac{2T}{2T + K_c d} \quad (15)$$

The response of the device can be viewed as a ratio of the force on the center sensor and the average force on the side sensors.

FIGS. 2A and 2B illustrate device 200A configured for tension measurement, according to one example. Device 200A includes detector 220A and handle 210.

Detector 220A includes frame 260A and force sensors 264A, 264B, and 264C each carried in a respective channel in frame 260A. Sensors 264A, 264B, and 264C include pins configured to move axially in channels 262A, 262B, and 262C and each pin is urged outward from frame 260A by an elastic member, here shown as springs disposed in channels 262A, 262B, and 262C.

Device 200A can be fabricated of plastic or synthetic materials. Sensors 264A, 264B, and 264C can include metal or plastic pins.

In FIG. 2A, device 200A is shown near elongate member 240 suspended by terminal anchor 230. Anchor 230 can include surrounding bone structure or tissue. In FIG. 2A, sensors 264A, 264B, and 264C are shown in an unloaded position and are extended outward. In FIG. 2B, elongate member 240 is displaced by device 200A. Sensors 264A, 264B, and 264C are shown to have positions based on the force associated with the deflection shown.

Arrow 250A denotes the direction of movement of device 200A as it approaches elongate member 240 for purposes of measuring tension in FIG. 2A. As shown by arrow 250B, elongate member 240 is deflected in a radial direction relative to the elongate member 240 axis represented by the illustration in FIG. 2A.

Figure 2C:
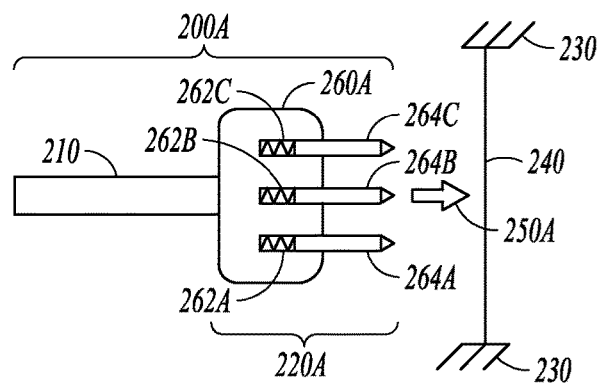
FIG. 2C illustrates a force sensor, according to one example.
Figure 2C:
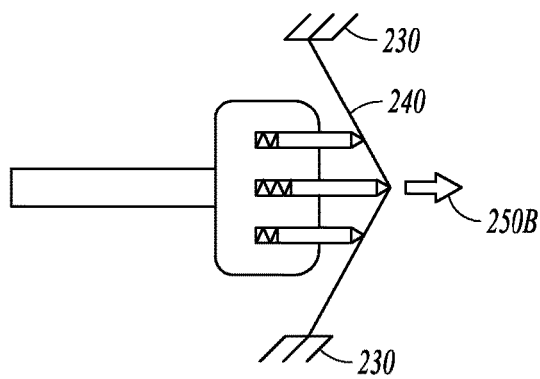
Figure 2C:
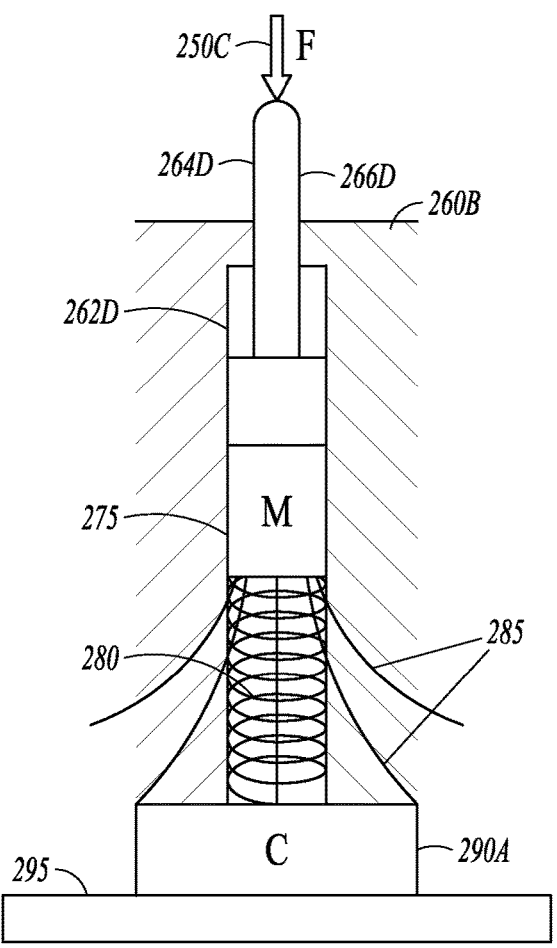

FIG. 2C illustrates force sensor 264D according to one example. Sensor 264D includes pin 266D extending from frame 260B (shown in cross-section). Pin 266D is allowed to travel axially in channel 262D and abuts magnet 275. Magnet 275 can be a permanent magnet. Spring 280 urges magnet 275 and pin 266D in an upward direction (in this view). A shoulder on pin 266D engages a feature of frame 260B and precludes ejection from frame 260B. Chip 290A is positioned below magnet 275 and is affixed to circuit board 295.

A force exerted on pin 266D in the direction indicated by arrow 250C can overcome spring 280 and allow magnet 275 to move closer to chip 290A. Chip 290A can include a magnetic encoder (such as a Hall effect encoder) and is responsive to the magnetic field lines 285 and provides an electrical output signal accordingly. In one example, chip 290A is electrically coupled to circuitry on circuit board 295.

According to one example, the spring constants of the side sensors (such as sensor 264C and sensor 264A) and center sensor (such as sensor 264B) can be 1.85 N/mm and 0.88 N/mm, respectively. The center-to-center distance of the adjacent force sensors can be 5 mm.

Force sensors 264A, 264B, and 264C are configured to apply a force at three points on elongate member 240. The reaction force compresses spring 280 (FIG. 2C) and allows magnet 275 to approach chip 290A. The displacement of magnet 275 causes an increase in the normal magnetic field incident on chip 290A and thus provide an electronic signal corresponding to the force applied.

An output signal from chip 290A can be influenced by a crosstalk arising from a magnetic field from a magnet in an adjacent force sensor. The effects of crosstalk among the force sensors can be mitigated. The polarity of one magnet can be reversed relative to the polarity of other nearby magnets to mitigate the effects of crosstalk. Other forms of compensation are also contemplated.

In one example of the present subject matter, the force applied to the elongate member is directed in a transverse direction. Detector 220A, having force sensors 264A, 264B, and 264C, is urged against the elongate member 240 with the plurality of sensors 264A, 264B, and 264C disposed on a single, or common, side. In one example, force sensors 264A, 264B, and 264C can measure tension in the range of 10 N to 120 N or in the range of 0 N to 150 N.

The relative forces measured by each of the force sensors can be correlated with displacement of a pin of that force sensor. A suitable deflection of the elongate member ensures accurate measurement of tension: if deflection is too small, then the sensor displacement is correspondingly small and the measurement accuracy suffers; similarly, if the deflection is too great, then the deflection will overwhelm or distort the tension and the measurement will be inaccurate. According to one example, a minimum sideways deflection of the elongate member of 0.1 mm, which corresponds to a displacement of a sensor contact surface of 0.1 mm, provides good measurement results.

In one example, a force sensor can include a load cell in combination with an elastic element (such as a spring).

Figure 3:
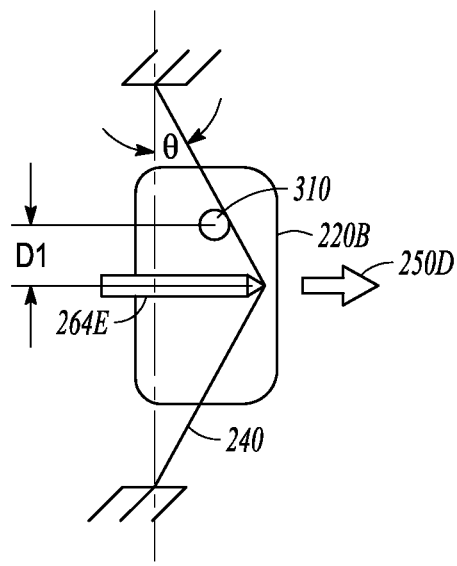
FIG. 3 illustrates a device for tension measurement, according to one example.

FIG. 3 illustrates detector 220B for tension measurement, according to one example. Detector 220B includes frame 260C configured to carrying force sensor 264E and feature 310. In the example illustrated, force sensor 264E includes a pin configured for axial movement (aligned parallel with arrow 250D) and configured to prevent radial movement.

Detector 220B can determine tension in elongate member 240 by applying a single transverse point force to the elongate member 240 and measuring the magnitude of force required to cause a fixed angular deflection in elongate member 240. Displacement of elongate member 240 relative to the undeflected position by force F (denoted by arrow 250D) causes deformation as indicated by angle θ. Assuming force F is applied at the midpoint of elongate member 240, tension T is determined by $$T = \frac{F}{2\sin\theta}$$

Thus, tension can be estimated based on measuring force F and angle υ.

As shown in FIG. 2B, an example detector includes three force sensors in which the center force sensor is taller than the two side force sensors. Assuming that the height difference in the force sensors is X, and the distance between the center force sensor and either side force sensor is d and that the bumps are rigid, then the angle made by the elongate member when the side force sensor just come into contact is given by:

$$\tan\theta = \frac{X}{d} \tag{16}$$

If the center force sensor is brought into contact with the midpoint of the elongate member, and the center force sensor is aligned normal with the natural position of the elongate filament, the two sides force sensors will come into contact with the elongate filament at the same instant of time. Accordingly, a detector can be fabricated with a single force sensor and an indicator to denote angle υ, as shown in FIG. 3.

In this example, the response of the detector would be determined by the force experienced by the taller force sensor when the elongate filament is deflected by a predetermined angle θ.

FIG. 3 illustrates an example detector. In one example, feature 310 includes a force sensor having sensitivity along an axis shown by arrow 250D. In one example, feature 310 includes a binary switch sensitive to contact by elongate member 240. In one example, feature 310 includes a strain gauge to indicate contact with elongate member 240. In one example, feature 310 includes a visual marker or visible calibration mark on a surface of frame 260C or other mechanism to indicate suitable displacement of elongate member 240. Distance D1 denotes a distance between feature 310 and force sensor 264E and is comparable to distance d noted in the equation above.

Figure 4:
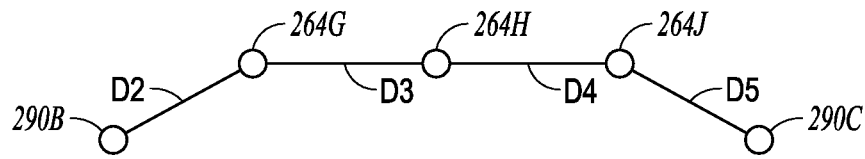
FIG. 4 illustrates an array of force sensors for tension measurement, according to one example.

FIG. 4 illustrates a view of an array of force sensors for tension measurement, according to one example. In the figure, chip 290B, force sensors 264G, 264H, and 264J, and chip 290C represent a configuration of sensors arranged to compensate for artifacts arising from nearby magnetic fields. In this example, each of chip 290B, force sensors 264G, 264H, and 264J, and chip 290C are separated by distances D2, D3, D4, and D5 as shown. Earlier examples described a configuration of three force sensors (see, for example, FIG. 2A). In the configuration shown in FIG. 4, chip 290B and chip 290C are used to reduce or cancel the effects of magnetic crosstalk.

Multiple moving magnets in a detector can produce an undesirable artifact referred to as magnetic crosstalk between nearby force sensor. The accuracy of the detector can be improved by addressing magnetic crosstalk.

Magnets of opposite polarity are used in force sensor 264G and force sensor 264J. Consequently, the magnetic chips used to read their magnetic field signals are also configured to read signals of opposite polarity. Hence, the motion of the magnet in force sensor 264H causes equal and opposite changes in force sensor 264G and force sensor 264J. Since the readings in force sensor 264G and force sensor 264J are averaged to obtain the sensor response ratio, the motion of the magnet in force sensor 264H does not result in any crosstalk on the magnets of force sensor 264G and force sensor 264J.

Magnetic sensing chips 290B and 290C can mitigate the influence of magnets in force sensor 264G and force sensor 264J on the chip in force sensor 264H. Consider the following approach.

Chip 290B, force sensors 264G, 264H, and 264J, and chip 290C are configured in such a way so that the distance D2 is equal to D3 and so that distance D4 is equal to D5 while maximizing the distance between chip 290B and force sensor 264H and while maximizing the distance between chip 290C and force sensor 264H to reduce the effect of the magnet of force sensor 264H on either of chip 290B and chip 290C.

Sensor elements are distributed in a configuration to maintain a short overall length and yet provide good compensation. In the figure, the compensating force sensors are offset from a straight line to reduce the overall detector length.

Figures 5, 6:
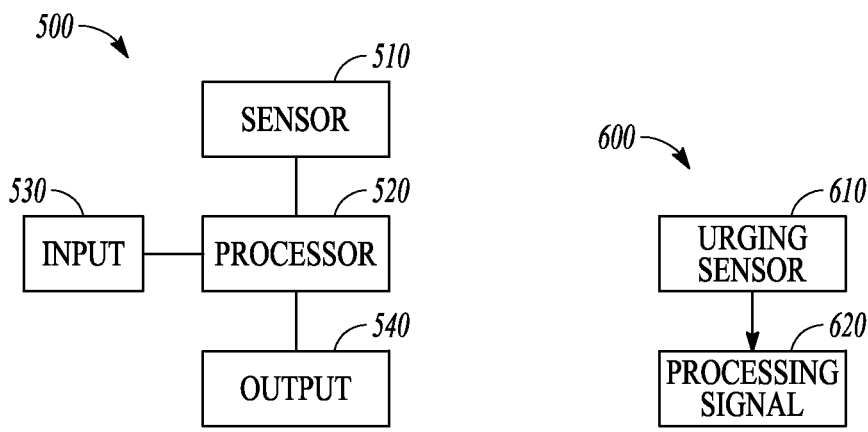
FIG. 5 illustrates a block diagram of a device, according to one example.
FIG. 6 illustrates a flow chart of a method, according to one example.

FIG. 5 illustrates a block diagram of device 500, according to one example. Device 500 includes force sensor module 510, processor 520, input module 530, and output module 540. Device 500 can be electrically powered by a battery or by a metered line service.

Force sensor module 510 can include one, two, three, four, five or more discrete force sensors as described elsewhere in this document. In the case of multiple force sensors, any two force sensors can be of different types. For example, one force sensor can include a moving magnet and another force sensor of the same detector can include a capacitance sensor. A capacitance sensor can provide a measure of force based on changes in spacing between parallel electrically conductive electrodes (plates) separated by an elastic dielectric.

Other types of force sensors are also contemplated. For example, a force sensor can include a piezoresistive sensor, a piezoelectric sensor, an inductive sensor, and a strain gauge.

Processor 520 can include a digital signal processor or an analog signal processor. In one example, processor 520 includes a digital processor configured to execute a set of instructions in order to perform a method as described herein.

In one example, input module 530 includes a user operable interface to allow a user to calibrate or control operation of device 500. Output module 540 can include a visible display or an audio transducer. In various examples, one or both of input module 530 and output module 540 includes a network interface configured to exchange instructions or data with a communication network.

FIG. 6 illustrates a flow chart of method 600, according to one example. In the example, method 600 includes, at 610, urging one or more force sensors against an elongate member. At 620, method 600 includes processing a signal from one or more force sensors to determine a measure of tension. Method 600 can be implemented in digital hardware or analog hardware.

VARIOUS NOTES & EXAMPLES

A number of the examples described earlier include device configurations include pushing a device against an elongate member in order to displace the elongate member and generate a measurable compressive force using a force sensor. In addition to this configuration, other examples can include a hook or other engagement feature in which a device is pulled away from an elongate member in order to determine a measure of tension. Accordingly, a force sensor can include a sense mechanism responsive to a tensile force rather than a compressive force.

A number of the examples described earlier include device configurations including linear movement of an element of a force sensor (e.g., a pin). In addition, a force sensor can be configured for non-linear movement. For example, a contact surface of a force sensor can be configured to travel on an arc determined by a pivot location. A force sensor can include a sense element that follows an arc or curved path.

In various examples, the contact surface of a force sensor is notched or otherwise configured to engage the elongate filament. One example includes a force sensor having a sensing pin with one or more projection or one or more depressions.

An elongate member can include a tissue, a filament, a tendon, or a ligament. In addition, an example of the present subject matter can be used for measuring tension in a wire, a cable, a textile, a web, a belt, a line, a rope, and other elongate members.

An example of the present subject matter can be configured as a handheld device. A handle can be coupled to the detector with an alignment suited for a particular application. For example, a handle can be aligned to engage a detector in a perpendicular, parallel, angled, or offset configuration in order to accommodate open surgery or minimally invasive surgical application. One example can be configured for a minimally-invasive arthroscopic application. A handheld miniaturized device, according to the present subject matter, can be inserted via a arthroscope during minimally-invasive orthopedic shoulder, knee and other surgeries. One example of a detector can be configured for coupling to a robotic manipulator.

One example of the present subject matter includes a force sensor (transducer) carried in a frame. Transducer provides an output signal based on the force exerted on contact face. A force sensor can be configured as a pin having sensitivity associated with pin movement in an axial direction or as a cantilever arm having sensitivity associated with translational movement of a free end relative to a fixed end.

Other configurations are also contemplated. For example, a strain gauge can be configured to provide a measure of force associated with a tensile load or a compressive load. A strain gauge provides an output corresponding to a detected strain arising from a force exerted on a surface.

One example allows measurement of tension by way of access on single side of the elongate member. In a surgical setting, a measure of tension can be generated by access on a single side or face of the elongate member.

In one example including three force sensors, the present subject matter can provide good data even if the detector is not precisely located at the center of the elongate filament.

In the case of a detector having two force sensors, the sense axes need not be precisely parallel. As such, the second force sensor can serve as a binary switch and even if not parallel but oriented in some other fashion (for instance perpendicular to the line joining the first and second sensor) the results can be satisfactory.

In the case of a detector having three force sensors, and calculating the tension based on a ratio of the center force to side forces, the three sense axis should be in parallel alignment.

In one example, a force sensor can include a linear bearing or bushing to reduce frictional effects in the system. A linear bearing can include a polished or lubricated surface to enable low resistance travel of a sense element in a force sensor.

Example 1 can include or use subject matter such as a device which can include a first sensor configured to generate a first signal corresponding to a detected first force, a second sensor configured to generate a second signal corresponding to a detected second force, wherein the first force and the second force have a substantially common direction, and a processor configured to determine a measure of tension using the first signal and using the second signal, wherein the measure of tension corresponds to displacement of an elongate member.

Example 2 can include, or can optionally be combined with the subject matter of Example 1, to optionally include a user operable handle coupled to the first sensor and the second sensor.

Example 3 can include, or can optionally be combined with the subject matter of Example 1 or Example 2, wherein the second sensor optionally includes a switch.

Example 4 can include, or can optionally be combined with the subject matter of one or any combination of Example 1 to Example 3 to optionally include wherein at least one of the first sensor and the second sensor includes a Hall effect sensor or a capacitive sensor.

Example 5 can include, or can optionally be combined with the subject matter of one or any combination of Example 1 to Example 4 to optionally include a third sensor configured to generate a third signal corresponding to a detected third force, the first force and the third force having a substantially common direction and wherein the processor is configured to determine the measure of tension using the third signal.

Example 6 can include, or can optionally be combined with the subject matter of Example 5 to optionally include wherein at least one of the first sensor, the second sensor, and the third sensor includes a movable magnet.

Example 7 can include, or can optionally be combined with the subject matter of one or any combination of Example 5 to Example 6 to optionally include wherein each of the first sensor, the second sensor, and the third sensor includes a movable magnet and wherein one movable magnet has a polarity alignment that differs from two other movable magnets.

Example 8 can include, or can optionally be combined with the subject matter of one or any combination of Example 5 to Example 7 to optionally include wherein the first sensor and the second sensor are spaced apart by a first distance and the second sensor and the third sensor are spaced apart by a second distance and wherein the first distance and the second distance are substantially equal.

Example 9 can include, or can optionally be combined with the subject matter of one or any combination of Example 5 to Example 8 to optionally include a fourth sensor configured to generate a fourth signal corresponding to a detected fourth force, the first force and the fourth force having a substantially common direction and wherein the processor is configured to determine the measure of tension using the fourth signal.

Example 10 can include, or can optionally be combined with the subject matter of Example 9 to optionally include a fifth sensor configured to generate a fifth signal corresponding to a detected fifth force, the first force and the fifth force having a substantially common direction and wherein the processor is configured to determine the measure of tension using the fifth signal.

Example 11 can include or use subject matter such as a method of measuring tension in an elongate member, such as can include or use urging a force sensor against the elongate member in a sense direction, the sense direction aligned substantially perpendicular to an axis of the elongate member, the force sensor configured to provide an output signal corresponding to a force in the sense direction at a time when the elongate member is radially displaced by a predetermined distance; and processing the output signal to determine a tensile force in the elongate member.

Example 12 can include or can optionally be combined with the subject matter of Example 11 to optionally include wherein urging the force sensor against the elongate member includes urging a plurality of force sensors along the sense direction.

Example 13 can include or can optionally be combined with the subject matter of Example 12 to optionally include wherein urging includes deflecting an elastic member of at least one force sensor.

Example 14 can include or can optionally be combined with the subject matter of one or any combination of Example 12 and Example 13 to optionally include wherein urging includes displacing a first force sensor and a second sensor by a substantially equal amount.

Example 15 can include or can optionally be combined with the subject matter of Example 11 to optionally include wherein processing includes executing instructions using a processor.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A handheld medical device comprising:
   a first sensor configured to generate a first signal corresponding to a detected first force when manually urged against a first location of an elongate member under tension, the elongate member comprising anatomical tissue;
   a second sensor configured to generate a second signal corresponding to a detected second force when manually urged against a second location of the elongate member;
   a third sensor configured to generate a third signal corresponding to a detected third force when manually urged against a third location of the elongate member, the first force, the second force, and the third force having a common direction substantially normal to an axis of the elongate member, wherein the first force, the second force, and the third force act against the elongate member simultaneously;
   a user operable handle coupled to the first sensor, the second sensor, and the third sensor; and
   a processor configured to determine the tension using the first signal, the second signal, and the third signal, the tension corresponding to deflection of the elongate member in a direction normal to the axis of the elongate member.

2. The medical device of claim 1, wherein the second sensor includes a switch.

3. The medical device of claim 1, wherein at least one of the first sensor, the second sensor, or the third sensor includes at least one of a Hall effect sensor or a capacitive sensor.

4. The medical device of claim 1, wherein at least one of the first sensor, the second sensor, or the third sensor includes a movable magnet.

5. The medical device of claim 1, wherein each of the first sensor, the second sensor, and the third sensor includes a movable magnet and wherein one movable magnet has a polarity alignment that differs from two other movable magnets.

6. The medical device of claim 1, wherein the first sensor and the second sensor are spaced apart by a first distance and the second sensor and the third sensor are spaced apart by a second distance and wherein the first distance and the second distance are substantially equal.

7. The medical device of claim 1, further including a fourth sensor configured to generate a fourth signal corresponding to a detected fourth force, the first force and the fourth force having a common direction substantially normal to the axis of the elongate member, and wherein the processor is configured to determine the measure of tension using the fourth signal.

8. The medical device of claim 7, further including a fifth sensor configured to generate a fifth signal corresponding to a detected fifth force, the first force and the fifth force having a common direction substantially normal to the axis of the elongate member, and wherein the processor is configured to determine the measure of tension using the fifth signal.

9. The medical device of claim 1, wherein the anatomical tissue of the elongate member comprises soft tissue of a patient, the soft tissue comprising one of muscle, fascia, tendon, ligament, or capsule.

10. The medical device of claim 1, wherein the elongate member comprises two ends, and wherein the two ends of the elongate member are fixed.

* * * * *